United States Patent [19]

Schisla et al.

[11] Patent Number: 5,427,717

[45] Date of Patent: Jun. 27, 1995

[54] SECONDARY ALKYL SULFATE/ZEOLITE-CONTAINING SURFACTANT COMPOSITIONS

[75] Inventors: David K. Schisla; Robert S. Tomaskovic; Eugene F. Lutz; Charles M. Arbore, all of Houston, Tex.

[73] Assignee: Shell Oil Company, Houston, Tex.

[21] Appl. No.: 198,677

[22] Filed: Feb. 18, 1994

Related U.S. Application Data

[63] Continuation of Ser. No. 990,920, Dec. 15, 1992, abandoned.

[51] Int. Cl.⁶ .......................... C11D 1/16; C11D 3/12
[52] U.S. Cl. ...................................... 252/549; 252/550; 252/171; 252/174.21; 252/174.25; 558/39; 558/42
[58] Field of Search ........... 252/549, 550, 171, 174.21, 252/174.25; 558/39, 42

[56] References Cited

U.S. PATENT DOCUMENTS

| | | | |
|---|---|---|---|
| 2,094,546 | 9/1937 | Lyons | 558/42 |
| 2,640,070 | 5/1953 | Dahmen | 558/42 |
| 2,945,818 | 7/1960 | Costine et al. | 252/550 |
| 3,234,258 | 2/1966 | Morris | 558/42 |
| 3,676,523 | 7/1972 | Mason | 252/428 |
| 3,681,424 | 8/1972 | Bloch et al. | 558/42 |
| 3,686,351 | 8/1972 | Mason | 252/428 |
| 3,737,475 | 6/1973 | Mason | 585/523 |
| 3,825,615 | 7/1974 | Lutz | 585/523 |
| 3,893,940 | 7/1975 | Ohogoshi et al. | 252/550 |
| 4,020,121 | 4/1977 | Kister et al. | 585/504 |
| 4,052,342 | 10/1977 | Fernley et al. | 252/550 |
| 4,088,598 | 5/1978 | Williams | 252/135 |
| 4,169,075 | 9/1979 | Kuhling et al. | 252/558 |
| 4,226,797 | 10/1980 | Bakker et al. | 558/42 |
| 4,322,367 | 3/1982 | Silvis | 558/36 |
| 4,474,678 | 10/1984 | Lutz et al. | 252/174.21 |
| 4,529,541 | 7/1985 | Wilms et al. | 252/550 |
| 4,544,493 | 10/1985 | Silvis | 252/549 |
| 4,605,509 | 8/1986 | Corkill et al. | 252/131 |
| 4,857,213 | 8/1989 | Caswell et al. | 252/551 |
| 4,923,636 | 5/1990 | Blackburn et al. | 252/550 |
| 5,026,400 | 6/1991 | Holland et al. | 252/174.21 |
| 5,039,453 | 8/1991 | Joshi et al. | 252/540 |
| 5,069,825 | 12/1991 | Joshi et al. | 252/533 |
| 5,075,041 | 12/1991 | Lutz | 252/548 |
| 5,080,820 | 1/1992 | Grecsek | 252/140 |
| 5,108,617 | 4/1992 | Eriksson et al. | 210/679 |
| 5,250,718 | 5/1993 | Lutz | 558/41 |
| 5,281,366 | 1/1994 | Lutz | 252/550 |
| 5,290,484 | 3/1994 | Lutz | 252/549 |

FOREIGN PATENT DOCUMENTS

| | | |
|---|---|---|
| 884656 | 12/1961 | United Kingdom . |
| 1194862 | 6/1970 | United Kingdom . |
| 1585030 | 5/1978 | United Kingdom . |

OTHER PUBLICATIONS

Asinger, "The Hydration of Olefins to Alcohols," Mono-olefins: Chemistry and Technology, 1968, pp. 689–704.

*Primary Examiner*—Paul Lieberman
*Assistant Examiner*—Kery A. Fries
*Attorney, Agent, or Firm*—Pamela J. McCollough

[57] ABSTRACT

This invention relates to solid secondary alkyl sulfate/zeolite-containing surface active compositions which are formed by crystallization and which contain at least about 80 percent by weight of secondary alkyl sulfate and zeolite. These compositions are substantially free of unreacted organic matter and water. The invention further relates to a process for preparing these solid secondary alkyl sulfate/zeolite-containing compositions.

35 Claims, No Drawings

SECONDARY ALKYL SULFATE/ZEOLITE-CONTAINING SURFACTANT COMPOSITIONS

This is a continuation of application Ser. No. 990,920, filed Dec. 15, 1992, now abandoned.

FIELD OF THE INVENTION

This invention relates to solid secondary alkyl sulfate/zeolite-containing surfactant compositions and to a process for preparing the compositions.

BACKGROUND OF THE INVENTION

In conventional practice, secondary alkyl sulfates have been prepared by reaction of olefins or alcohols with sulfuric acid followed by neutralization of the intermediate secondary alkyl sulfuric acid with aqueous base, usually sodium hydroxide. The process is complicated by incomplete reaction of the starting olefin or alcohol and by formation of dialkyl sulfates which saponify during the neutralization step, noted above, to equal molar amounts of secondary alkyl sulfate and secondary alcohol.

Unreacted olefin and secondary alcohol, which can amount to 50% by weight or more of the starting olefin, are generally removed from the secondary alkyl sulfate by a process of extraction with an organic solvent as described in U.S. Pat. No. 4,175,092. The extraction process can be complicated by the formation of undesirable emulsions and gels as well as by the dissolution of some of the extracting solvent in the aqueous secondary alkyl sulfate phase. Extracting solvents frequently have objectionable odors and must be removed from the aqueous surfactant solution, an operation which can be accompanied by severe foaming difficulties. When extraction is complete, the concentration of secondary alkyl sulfate in water is generally in the range of 20–40% by weight (F. Asinger, *Mono-Olefins: Chemistry and Technology*, 1968, pp. 689–694).

It would therefore be advantageous to isolate solid secondary alkyl sulfate in a form compatible with surfactant compositions which are substantially free of water and unreacted organic matter, thus allowing maximum handling flexibility. Solid secondary alkyl sulfate compositions and a process for their preparation is taught in copending application Ser. No. 90,056, filed May 28, 1992, the contents of which are incorporated herein by reference. In addition, it would be advantageous to have a product into which a zeolite has been incorporated because a product containing both anionic surfactant and zeolite could simplify detergent formulation.

A process for preparing surfactant compositions has been found in which secondary alkyl sulfates derived from olefins and/or alcohols can be generated in a manner such that the secondary alkyl sulfate/zeolite-containing product is a solid which can be used as a surfactant and/or a detergent composition which is particularly suitable for household applications.

SUMMARY OF THE INVENTION

This invention relates to a secondary alkyl sulfate/zeolite product and a process for preparing a solid secondary alkyl sulfate/zeolite-containing surface active composition which comprises preparing a detergent range alkyl sulfuric acid-containing solution, contacting the sulfuric acid-containing solution with a base in aqueous solution, heating to saponify and to remove substantially all of the water from the mixture, adding a nonionic organic liquid diluent, cooling to crystallize a solid secondary alkyl sulfate-containing surface active composition from the reaction mixture, incorporating a zeolite and recovering and drying the crystallized solid secondary alkyl sulfate/zeolite-containing surface active composition.

The invention further relates to solid secondary alkyl sulfate/zeolite-containing surface active compositions prepared by crystallization which are substantially free of water and unreacted organic matter and which comprise at least about 80 percent by weight of secondary alkyl sulfate and zeolite, basis the total weight of the composition.

DESCRIPTION OF THE PREFERRED EMBODIMENTS

The invention provides solid secondary alkyl sulfate/zeolite-containing surfactant compositions as well as a process for preparing solid secondary alkyl sulfate/zeolite-containing surfactant compositions which are substantially free of unreacted organic matter (UOM) and water. These solid surface active compositions are prepared by a process which in its broadest aspect comprises preparing a detergent range alkyl sulfuric acid-containing solution, contacting the detergent range alkyl sulfuric acid-containing solution with a base in aqueous solution, heating to remove substantially all of the water from the mixture, cooling in the presence of a nonionic organic liquid diluent to crystallize a solid secondary alkyl sulfate-containing surface active composition from the mixture, incorporating a zeolite into the composition, and recovering and drying the crystallized secondary alkyl sulfate/zeolite-containing product, thereby producing a solid secondary alkyl sulfate/zeolite-containing surfactant composition which is typically a free flowing powder, which is anhydrous and which is substantially free of diluents.

The present invention therefore relates to solid secondary alkyl sulfate-containing surface active compositions, typically free flowing powders which are substantially free of unreacted organic matter and water, prepared by a process which comprises the steps of: a) sulfating a reactant selected from the group consisting of detergent range olefins, detergent range alcohols and mixtures thereof, b) neutralizing the sulfation product of step a) with a base in aqueous solution, c) saponifying the product of step b), d) crystallizing the product of step c), and e) recovering and drying the secondary alkyl sulfate/zeolite-containing product from the product of step d), wherein a nonionic organic liquid diluent is added in step a), step b), step c) or a combination of these steps, and wherein a zeolite is added in step c), or step d), following step e), or a combination of these steps.

As used herein, the phrase "substantially free of unreacted organic matter and water" refers to compositions which contain less than about 10 percent by weight, preferably less than about 5 percent by weight, of unreacted organic matter and less than about 5 percent by weight, preferably less than about 2 percent by weight, of water.

The detergent range alkyl sulfuric acid-containing solution in step a) of the present process can be prepared by sulfation of detergent range olefins, detergent range alcohols or a mixture of detergent range olefins and alcohols. In a preferred embodiment, the detergent range alkyl sulfuric acid-containing solution is prepared by the sulfation of detergent range olefins or by the sulfation of a mixture of detergent range olefins and detergent range alcohols.

The detergent range olefins which are suitable for use in the preparation of the detergent range alkyl sulfuric acid-containing solution are olefins containing from about 8 to about 22 carbon atoms. These olefins can be alpha olefins or internal olefins and they may be linear or branched, but are preferably linear or lightly branched. Single cut olefins or mixtures of olefins may also be used. In a particularly preferred embodiment, the olefin contains from about 12 to about 18 carbon atoms.

Preferred olefins for use in the preparation of the alkyl sulfuric acid-containing solution for the practical reason of availability are the commercial olefin products in the $C_8$ to $C_{22}$ range. While commercial production of such olefins may be carried out by the cracking of paraffin wax, commercial production is more commonly accomplished by the oligomerization of ethylene using procedures well known in the art. The resulting oligomerization products are substantially of linear structure and thus products are substantially of linear structure. Commercial olefin products manufactured by ethylene oligomerization are marketed in the United States by Shell Chemical Company under the trademark NEODENE and by Ethyl Corporation as Ethyl Alpha-Olefins. Specific procedures for preparing suitable linear olefins from ethylene are described in U.S. Pat. Nos. 3,676,523, 3,686,351, 3,737,475, 3,825,615 and 4,020,121, the teachings of which are incorporated herein by reference. While most of such olefin products are comprised largely of alpha-olefins, higher linear internal olefins are also commercially produced, for example, by the chlorination-dehydrochlorination of paraffins, by paraffin dehydrogenation, and by isomerization of alpha-olefins. Linear internal olefin products in the $C_8$ to $C_{22}$ range are marketed by Shell Chemical Company and by Liquichemica Company. These commercial products, whether predominantly internal or alpha-olefins typically contain about 70 percent by weight or more, most often about 80 percent by weight or more, linear mono-olefins in a specified carbon number range (e.g., $C_{10}$ to $C_{12}$, $C_{11}$ to $C_{15}$, $C_{12}$ to $C_{13}$, $C_{15}$ to $C_{18}$, etc.), the remainder of the product being olefin of other carbon number or carbon structure, diolefins, paraffins, aromatics, and other impurities resulting from the synthesis process. Olefins in the $C_{12}$ to $C_{18}$ range are considered most preferred for use in the instant invention.

The detergent range alcohols which are suitable for use in the preparation of the detergent range alkyl sulfuric acid-containing solution are alcohols containing from about 8 to about 22 carbon atoms. Acyclic aliphatic alcohols (alcohols) having from about 9 to about 18 carbon atoms form a preferred class of reactants, particularly the secondary alcohols, as secondary alcohols make up a portion of the potential recycle stream in the present process, although primary alcohols can also be utilized. When primary alcohols are utilized in combination with olefins and/or secondary alcohols, the product obtained will be a mixture of primary alkyl sulfates and secondary alkyl sulfates. As a general rule, the alcohols may be of branched or straight chain structure, although alcohol reactants in which greater than about 50 percent, more preferably greater than about 60 percent, and most preferably greater than about 70 percent of the molecules are of linear (straight-chain) carbon structure are preferred.

When mixtures of detergent range olefins and detergent range alcohols are used in the preparation of the detergent range alkyl sulfuric acid-containing solution, the mixture suitably comprises from about 40 percent to about 90 percent detergent range olefins and from about 10 percent to about 60 percent detergent range alcohols. A preferred mixture includes from about 60 percent to about 80 percent detergent range olefins and from about 20 percent to about 40 percent detergent range alcohols.

The sulfating agents suitable for use in preparing the alkyl sulfuric acid-containing solution in step a) include those compounds capable of forming the carbon to oxygen to sulfur bonds necessary for the formation of an alkyl sulfate. The particular sulfating agents used are typically a function of the compounds to be sulfated. These sulfating agents are known in the art and include sulfuric acid or sulfuric acid salts for the sulfation of olefins, and sulfur trioxide, chlorosulfonic acid or oleum for the sulfation of alcohols. In a preferred embodiment, the alkyl sulfuric acid-containing solution is derived from the sulfation of detergent range olefins or a mixture of detergent range olefins and detergent range alcohols and the sulfating agent is concentrated sulfuric acid.

When concentrated sulfuric acid is used to sulfate detergent range olefins or a mixture of detergent range olefins and detergent range alcohols, the concentrated sulfuric acid is typically from about 75 percent by weight to about 100 percent by weight, preferably from about 85 percent by weight to about 98 percent by weight, in water. Suitable amounts of sulfuric acid are generally in the range of from about 0.3 mole to about 1.3 moles of sulfuric acid per mole of olefin and/or alcohol, preferably from about 0.4 mole to about 1.0 mole of sulfuric acid per mole of olefin and/or alcohol.

The sulfation reaction which results in the alkyl sulfuric acid-containing solution is typically carried out at temperatures in the range of from about $-20°$ C. to about $50°$ C., preferably from about $5°$ C. to about $40°$ C., and at pressures in the range of from about 1 atmosphere to about 5 atmospheres, preferably from about 1 atmosphere to about 2 atmospheres, and more preferably, about 1 atmosphere. Suitable residence times for the sulfation reaction range from a few minutes to several hours, preferably from about 2 minutes to about 10 hours and more preferably, from about 5 minutes to about 3 hours.

The sulfation reaction for a detergent range olefin may be illustrated by the following equation:

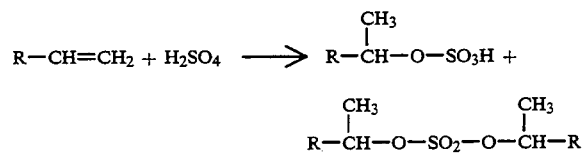

wherein R is an alkyl group having from about 6 to about 20 carbon atoms. The sulfation reaction results in an alkyl sulfuric acid-containing solution. As used herein, the term "alkyl sulfuric acid-containing solution" is used to refer to all of the products of the sulfation reaction which include primarily monoalkyl sulfuric acids and dialkyl sulfates along with unreacted olefin and unreacted sulfuric acid.

In one embodiment, the alkyl sulfuric acid-containing solution may, prior to the contact with an aqueous solution of a base in step b) or prior to neutralization, be subjected to deacidification for the partial or substantially complete removal of any unreacted sulfuric acid or any other unreacted sulfating agent. Suitable deacidification procedures include washing the sulfation reaction product with water or an acid such as sulfuric acid having a concentration of from about 75 percent by weight to about 90 percent by weight, preferably from about 80 percent by weight to about 85 percent by weight, in water. The deacidification is typically carried out at the same temperature at which the sulfation reaction is carried out. While it is not critical that the alkyl sulfuric acid-containing solution be subjected to deacidification, in a preferred embodiment, the alkyl sulfuric acid-containing solution is deacidified by the addition of small amounts of sulfuric acid thereto in order to remove as much unreacted sulfating agent as possible.

In the present process, the nonionic organic liquid diluent can be added during the sulfation step (step a)), during the neutralization step (step b)), during the saponification step (step c)), or during a combination of any or all of these steps, provided the diluent is substantially inert in the particular step or steps in which it is added. It is not critical at what point the nonionic organic liquid diluent is added as long as the diluent is present prior to crystallization.

The nonionic organic liquid diluent in the present process is typically an aliphatic or aromatic hydrocarbon, but can be any composition which will permit secondary alkyl sulfate precipitation. As used herein, the term "nonionic organic liquid diluent" is used to refer to a composition having characteristics such that the secondary alkyl sulfate product precipitates from solution. The nonionic organic liquid diluent, if inert to the specific step in the reaction sequence, may be added along with the detergent range olefins and/or alcohols at the beginning of the sulfation step, at any point during the sulfation step, after the sulfation reaction is completed, following the deacidification step, or, it may be contacted with the alkyl sulfuric acid-containing solution during contact of the solution with the aqueous solution of base. Alternatively, the nonionic organic liquid diluent may be added at more than one of the above-mentioned places in the process, provided it is substantially inert in the place in which it is added. In a preferred embodiment, the nonionic organic liquid diluent is added to the alkyl sulfuric acid-containing solution following the sulfation step. Suitable nonionic organic liquid diluents include heptane, toluene, isooctane, nonane and mixtures thereof, with preference being given to heptane and isooctane, particularly heptane. While not wishing to be bound by any particular theory, it is believed that the function of the nonionic organic liquid diluent in the present process is to provide a medium in which unreacted organic matter is soluble and secondary alkyl sulfate, at least in part, is not.

The alkyl sulfuric acid-containing solution and the nonionic organic liquid diluent, if added during the sulfation step, are contacted with an aqueous solution of a base in order to neutralize the alkyl sulfuric acid portion of the sulfuric acid-containing solution to form the corresponding sulfuric acid salts.

The neutralization reaction is accomplished using an aqueous solution of one or more bases such as ammonium or alkali metal or alkaline earth metal hydroxides or carbonates or bicarbonates. Suitable bases include sodium hydroxide, sodium carbonate, potassium hydroxide, calcium hydroxide and the like, with sodium hydroxide or potassium hydroxide being the preferred base. The concentration of the aqueous solution of base is suitably from about 10 percent by weight to about 85 percent by weight base, preferably from about 15 percent by weight to about 75 percent by weight, and more preferably from about 20 percent by weight to about 50 percent by weight, in water. In a preferred embodiment, the base utilized is sodium hydroxide or potassium hydroxide, and the concentration of the aqueous solution of base is from about 10 percent by weight to about 75 percent by weight base, preferably from about 20 percent by weight to about 50 percent by weight, in water. Generally, an amount of base in excess of the amount required to neutralize the alkyl sulfuric acids and saponify the dialkyl sulfates is used. Suitable amounts of base are generally in the range of from about 1.2 moles to about 1 mole of base per equivalent of sulfuric acid, alkyl sulfuric acid and dialkyl sulfate, and preferably in the range of from about 1.1 moles to about 1.0 mole of base.

The neutralization procedure can be carried out over a wide range of temperatures and pressures. Typically, the neutralization procedure is carried out at a temperature in the range of from about 20° C. to about 65° C., and a pressure in the range of from about 1 atmosphere to about 2 atmospheres. The neutralization time is typically in the range of from about 0.2 hours to about 1.0 hours.

Following the contact in step b) of the alkyl sulfuric acid-containing solution and, optionally, the nonionic organic liquid diluent with an aqueous solution of a base to effect neutralization, the product of step b), is heated in step c) to a temperature in the range of from about 70° C. to about 115° C., preferably from about 80° C. to about 105° C. in order to effect saponification or hydrolysis of the dialkyl sulfates to form alkyl sulfuric acid salts and secondary alcohols and remove substantially all of the water from the product of step b). In this step, water is azeotropically distilled to remove a liquid containing a water phase and a nonionic organic liquid diluent phase. The nonionic organic liquid diluent phase is returned to the reaction vessel and the water phase is discarded. This step is typically carried out using a Dean Stark trap or another similar device.

The saponification procedure can be carried out over a wide range of temperature and pressures. The saponification procedure is typically carried out at a temperature in the range of from about 80° C. to about 105° C. and a pressure of from about 1 atmosphere to about 2 atmospheres. The saponification reaction is generally carried out over a time period ranging from about 0.25 hours to about 5.0 hours.

The neutralization and saponification reactions may be illustrated by the following equations:

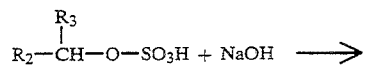

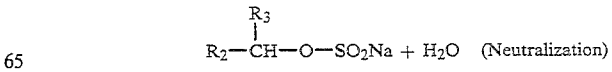

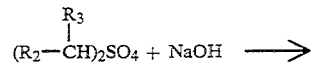

-continued

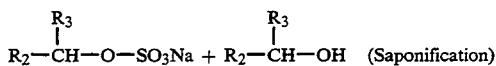

wherein $R_2$ and $R_3$ are alkyl groups having from about 1 to about 20 carbon atoms.

The zeolites suitable for use in the present invention are typically those zeolites which are suitable for use as builders in detergent compositions. As used herein, the term "zeolite" is used to refer to crystalline aluminosilicate minerals of a cage-network structure with pores a few angstroms in diameter. Some of the common materials, such as zeolite Y (faujasite) or zeolite A have a three dimensional structure with pore intersections ("supercages") somewhat larger than the pore size. Others such as zeolite L and mordenite have channels. For each type of zeolite a theoretical crystal structure or "framework" can be specified which is composed of interconnected silicon atoms, aluminum atoms and oxygen atoms arranged in an ordered fashion. The aluminum found within the framework is referred to as "framework aluminum". A typical zeolitic framework comprises corner-sharing $SiO_4$ and $AlO_4$ tetrahedra. Excess negative charges in the Si—O—Al framework are balanced by the presence of suitable positive ions such as hydrogen, ammonium, alkali metal, alkaline earth metal, rare earth metal, etc. Each specific zeolite will have either a specific Si to Al ratio or specified range of Si to Al ratios that correspond to the theoretical crystal structure of such zeolite type.

Zeolites which are suitable for use in the present invention are zeolite A, zeolite Y, zeolite Z and mixtures thereof, with zeolite A being particularly preferred. Zeolite A is commercially available from sources such as The PQ Corporation under the trademark VALFOR 100, and the Ethyl Corporation. The amount of zeolite used in the present process is typically an amount such that the final secondary alkyl sulfate/zeolite composition contains at least about 25 percent by weight, preferably from about 50 percent by weight to about 75 percent by weight zeolite, basis the total weight of the composition.

The zeolite may be added during the saponification step (step c), during the crystallization step (step d), or following the crystallization step. The zeolite is believed to act as a filter aid in the recovery of the secondary alkyl sulfate/zeolite-containing product. It is also within the scope of the present invention to add the zeolite in a combination of steps such as, for example, the zeolite can be added prior to crystallization, during crystallization and following crystallization. In a preferred embodiment, the zeolite is added after crystallization due to practical considerations.

Following saponification and removal of substantially all of the water, the resulting product is then cooled to a temperature in the range of from about 20° C. to about 85° C. in the presence of the nonionic organic liquid diluent to effect crystallization of the solid secondary alkyl sulfate from the saponified product of step c). The cooling step generally takes place over a period of about 0.25 hours to about 18 hours, preferably about 0.5 hours to about 16 hours, although both shorter and longer time periods are also acceptable. During the cooling step, the solubility of secondary alkyl sulfate is further reduced and additional secondary alkyl sulfate solids are formed.

The crystallized secondary alkyl sulfate/zeolite product is then recovered and dried as solid secondary alkyl sulfate/zeolite-containing composition. The secondary alkyl sulfate/zeolite crystals can be recovered by filtration or centrifugation. The crystallized secondary alkyl sulfate/zeolite-containing product is typically dried at temperatures in the range of from about 40° C. to about 80° C. using nitrogen-swept vacuum or other conventional drying means. Prior to drying, the crystals may be subjected to washing with the particular nonionic organic liquid diluent utilized or with any other conventional washing agent in order to increase the purity of the secondary alkyl sulfate/zeolite-containing product.

The remainder of the product of step e) which contains unreacted starting material, secondary alcohol, and nonionic organic liquid diluent, as well as some uncrystallized secondary alkyl sulfate, may be recycled. Alternatively, the uncrystallized secondary alkyl sulfate may be removed from the product of step e), if desired, prior to recycle. In addition, if desired, the secondary alcohol can be separated from the unreacted starting material by means recognized by those skilled in the art such as, for example, distillation.

The process of the present invention may be carried out in a batch mode or in a continuous operation.

The solid secondary alkyl sulfate/zeolite-containing surfactant compositions prepared in the present process typically contain at least about 80 percent by weight of a combination of secondary alkyl sulfate and zeolite, basis the total weight of the composition, and preferably at least about 90 percent by weight of a combination of secondary alkyl sulfate and zeolite. The solid secondary alkyl sulfate/zeolite product produced contains at least about 25 percent by weight to about 75 percent by weight, preferably about 25 percent by weight to about 50 percent by weight of secondary alkyl sulfate, and at least about 25 percent by weight to about 75 percent by weight, preferably about 50 percent by weight to about 75 percent by weight of zeolite. The product generally contains some residual level of sodium sulfate. The product typically contains less than about 12 percent by weight, preferably less than about 9 percent by weight, sodium sulfate.

The surfactant compositions of the invention can be utilized in a variety of detergent applications. The surfactant compositions can be blended with solid detergent components such as, for example, sodium carbonate, in order to form dry detergent powders. The surfactant compositions can also be added to water or vice versa in order to form liquid detergents.

The ranges and limitations provided in the instant specification and claims are those which are believed to particularly point out and distinctly claim the present invention. It is, however, understood that other ranges and limitations which perform substantially the same function in substantially the same manner to obtain the same or substantially the same result are intended to be within the scope of the instant invention as defined by the instant specification and claims.

The invention will be described below by the following examples which are provided for purposes of illustration and are not to be construed as limiting the invention.

ILLUSTRATIVE EMBODIMENTS
EXAMPLE 1

To a three necked 2-liter jacketed glass vessel with a paddle stirrer, thermometer, and addition flask topped with a nitrogen blanket was added 400 grams of 97% weight $C_{16}$ linear alpha olefin. Glycol chilled to 0° C. was circulated through the vessel jacket. 115 Grams of 95% weight sulfuric acid were added with good agitation at a rate such that the temperature did not exceed 20° C. When the addition of sulfuric acid was complete, the mixture was agitated for about 1 hour. 200 Grams of heptane were then added to the mixture. 500 Grams of this mixture were then added to 212.5 grams of 20% weight NaOH in a second three necked 2-liter glass vessel equipped with a paddle stirrer, thermometer, a Dean-Stark trap with a nitrogen blanket, and an additional flask. The temperature in the reaction flask rose from about 24° C. to 70° C. during acid neutralization. When the acid addition was complete, 150 grams of heptane was added to this mixture.

The addition flask was replaced with a nitrogen blanketed Dean Stark trap and the reactor was heated to azeotropically distill the water from the reaction mixture. After 172 grams of water were removed and the reaction temperature reached 100° C., 50 grams of the zeolite VALFOR 100 (VALFOR is a trademark of and sold by The PQ Corporation) were added to the reaction mixture. An additional 50 grams of heptane were also added to the reaction mixture. After azeotropically distilling another 16 grams of water, for a total of 188 grams, heating was discontinued and the heptane in the Dean Stark trap was returned to the reactor.

On cooling overnight to room temperature, the reactor contents were filtered using a 10 centimeter diameter Buchner funnel. The solid isolated on the filter was washed with 1200 grams of heptane. The solid product was then transferred to a tared dish and dried at 60° C. and in a nitrogen swept vacuum of 22 inches of mercury to a constant weight. The dried solid product weighed 193.8 grams. Analysis showed the recovered product to be 75.0% weight anionic surfactant and 0.18% weight sodium sulfate. An analysis was not performed on the zeolite but all that was added was retained on the filter and hence in the solid product, which accounts for the remaining 25% of the product. The anionic surfactant yield was 35% mole (% m), basis starting olefin. The results are presented in Table I.

EXAMPLE 2

Example 2 was carried out in a manner similar to Example 1, except that 150 grams of VALFOR 100 were added instead of 50 grams. 288 Grams of the solid product were recovered, containing 53.8% weight anionic surfactant, 0.25% weight sodium sulfate, and about 50% weight zeolite. The anionic surfactant yield was 36%m basis starting olefin. The results are presented in Table I.

EXAMPLE 3

Example 3 was carried out in a manner similar to Examples 1 and 2, except that the zeolite was added after the reaction mixture, or slurry, was cooled to room temperature. The process leading up to zeolite addition makes a solid product containing primarily anionic surfactant, with smaller amounts of sodium sulfate and sodium hydroxide. In Example 3, 150 grams of heptane were added after neutralization instead of the 200 grams added in Example 1. 640 Grams of slurry were recovered. 214 Grams of the slurry were filtered without the addition of zeolite and washed with 404 grams of heptane to obtain 50.4 grams of a solid product containing 97.0% weight anionic surfactant and 0.34% weight sodium sulfate. 220 Grams of the slurry were blended with 100 grams of zeolite and this mixture was filtered and washed with 409 grams of heptane. 150 Grams of solid product were recovered which was 34.4% weight anionic surfactant and about 66% weight zeolite. The anionic surfactant yield on starting olefin for both cases was 36% m. Also, the filtration rates were not different, although the weight of the cake was about three times larger and the thickness of the cake was twice as large with the zeolite. The results are presented in Table I.

EXAMPLE 4

Example 4 was carried out in a similar manner to Example 3. Part of the slurry was blended with zeolite to give a solid product containing 35.5% weight anionic surfactant with the remaining balance primarily zeolite. The slurry was also filtered without adding zeolite to give a solid product containing 99.1% weight anionic surfactant and 1.3% weight sodium sulfate. The anionic surfactant yield on olefin was again the same for both cases at 38% m. However, in Example 4 the filtration rate was three times faster for the slurry containing zeolite. The results are presented in Table I.

TABLE I

| Example No. | Olefin and/or Alcohol (% wt.) | Acid/Olefin and/or Alcohol Ratio (mole/mole) | Diluent | Zeolite | Secondary Alkyl Sulfate Recovered as Solid (% m) | Secondary Alkyl Sulfate Purity | Zeolite in Product (% wt.) |
|---|---|---|---|---|---|---|---|
| 1 | $C_{16}$ | 0.62 | Heptane | VALFOR ® 100 | 35 | 75.0 | 25 |
| 2 | $C_{16}$ | 0.62 | Heptane | VALFOR ® 100 | 36 | 53.8 | 50 |
| 3 | $C_{16}$ | 0.62 | Heptane | VALFOR ® 100 | 36 | 34.4 | 66 |
| 4 | $C_{16}$ | 0.62 | Heptane | VALFOR ® 100 | 38 | 35.5 | 66 |

What is claimed is:

1. A process for preparing a solid secondary alkyl sulfate-containing surface active composition which comprises: a) preparing a detergent range alkyl sulfuric acid-containing solution, b) contacting said detergent range alkyl sulfuric acid-containing solution with a base in aqueous solution, c) heating the product of step b) to saponify dialkyl sulfate and to remove substantially all of the water from the mixture, d) cooling the product of step c) in the presence of a nonionic organic inert liquid diluent selected from the group consisting of aliphatic hydrocarbons, aromatic hydrocarbons, and mixtures thereof, to precipitate a crystallized solid secondary alkyl sulfate-containing surface active composition from the mixture, and e) recovering and drying the crystallized solid secondary alkyl sulfate-containing surface active composition, wherein a zeolite is added in step c), step d), following step d) or a combination of these steps, and wherein said nonionic organic liquid diluent is added in step a), step b), step c) or a combination of these steps.

2. The process of claim 1 wherein said detergent range alkyl sulfuric acid-containing solution is prepared by sulfating a reactant selected from the group consisting of detergent range olefins, detergent range alcohols and mixtures thereof, with a sulfating agent.

3. The process of claim 1 wherein the nonionic organic liquid diluent is selected from the group consisting of heptane, toluene, isooctane, nonane, and mixtures thereof.

4. The process of claim 1 wherein the nonionic organic liquid diluent is added in step a).

5. The process of claim 1 wherein the nonionic organic liquid diluent is added in step b).

6. The process of claim 1 wherein the nonionic organic liquid diluent is added in step c).

7. The process of claim 1 wherein the base in step b) is selected from ammonium, alkali metal or alkaline earth metal hydroxides, carbonates or bicarbonates.

8. The process of claim 7 wherein said base is selected from the group consisting of sodium hydroxide, potassium hydroxide and mixtures thereof.

9. The process of claim 1 wherein said base in aqueous solution comprises from about 10 percent by weight to about 85 percent by weight of base in water.

10. The process of claim 1 wherein said zeolite is selected from the group consisting of zeolite A, zeolite X, zeolite Y and mixtures thereof.

11. The process of claim 10 wherein said zeolite is zeolite A.

12. The process of claim 1 wherein the zeolite is added in step c).

13. The process of claim 1 wherein the zeolite is added in step d).

14. The process of claim 1 wherein the zeolite is added in step e).

15. The process of claim 1 wherein said solid secondary alkyl sulfate-containing surface active composition recovered in step e) contains from about 25 percent by weight to about 75 percent by weight secondary alkyl sulfate and from about 25 percent by weight to about 75 percent by weight zeolite.

16. A process for preparing a solid secondary alkyl sulfate-containing surface active compositions substantially free of unreacted organic matter and water, which process comprises: a) sulfating a reactant selected from the group consisting of detergent range olefins, detergent range alcohols and mixtures thereof, b) neutralizing the sulfation product of step a) with a base in aqueous solution, c) saponifying the product of step b) and removing substantially all of the water, d) crystallizing the product of step c), and e) recovering and drying the secondary alkyl sulfate-containing product from the product of step d), wherein a nonionic organic liquid diluent selected from the group consisting of aliphatic hydrocarbons, aromatic hydrocarbons, and mixtures thereof, is added in step a), step b), step c) or a combination of these steps, and wherein a zeolite is added in step c), step d), following step d) or a combination of these steps.

17. The process of claim 16 wherein said reactant is a detergent range olefin having from about 12 to about 18 carbon atoms.

18. The process of claim 16 wherein said sulfating step is carried out using concentrated sulfuric acid having a concentration of from about 75 percent by weight to about 100 percent by weight in water.

19. The process of claim 16 wherein said sulfating step is carried out at a temperature in the range of from about 5° C. to about 40° C. and a pressure in the range of from about 1 atmosphere to about 2 atmospheres.

20. The process of claim 16 wherein said base in step b) is selected from ammonium, alkali metal or alkaline earth metal hydroxides, carbonates or bicarbonates.

21. The process of claim 20 wherein said base is selected from the group consisting of sodium hydroxide, potassium hydroxide and mixtures thereof.

22. The process of claim 16 wherein said base in aqueous solution comprises from about 10 percent by weight to about 85 percent by weight base in water.

23. The process of claim 16 wherein said neutralization in step b) is carried out at temperatures in the range of from about 20° C. to about 65° C. and pressures in the range of from about 1 atmosphere to about 2 atmospheres.

24. The process of claim 16 wherein said saponification in step c) is carried out at a temperature in the range of from about 80° C. to about 105° C. and a pressure of from about 1 atmosphere to about 2 atmospheres.

25. The process of claim 17 wherein the nonionic organic liquid diluent is selected from the group consisting of heptane, toluene, isooctane, nonane, and mixtures thereof.

26. The process of claim 16 wherein the nonionic organic liquid diluent is added in step a).

27. The process of claim 16 wherein the nonionic organic liquid diluent is added in step b).

28. The process of claim 16 wherein the nonionic organic liquid diluent is added in step c).

29. The process of claim 16 wherein said product recovered in step e) contains from about 25 percent by weight to about 75 percent by weight secondary alkyl sulfate and from about 25 percent by weight to about 75 percent by weight zeolite.

30. The process of claim 16 wherein said zeolite is selected from the group consisting of zeolite A, zeolite X, zeolite Y and mixtures thereof.

31. The process of claim 27 wherein said zeolite is zeolite A.

32. The process of claim 16 wherein the zeolite is added in step c).

33. The process of claim 16 wherein the zeolite is added in step d).

34. The process of claim 16 wherein the zeolite is added following step d).

35. The process of claim 16 wherein said product recovered in step e) contains from about 25 percent by weight to about 75 percent by weight secondary alkyl sulfate and from about 25 percent by weight to about 75 percent by weight zeolite.

* * * * *